United States Patent
Yagita

(10) Patent No.: US 7,342,655 B2
(45) Date of Patent: Mar. 11, 2008

(54) INSPECTING APPARATUS AND METHOD FOR FOREIGN MATTER

(75) Inventor: Kiyoshi Yagita, Tokyo (JP)

(73) Assignee: Scan Technology Co., Ltd., Tokyo (JP)

( * ) Notice: Subject to any disclaimer, the term of this patent is extended or adjusted under 35 U.S.C. 154(b) by 195 days.

(21) Appl. No.: 11/181,704

(22) Filed: Jul. 13, 2005

(65) Prior Publication Data

US 2006/0244959 A1 Nov. 2, 2006

(30) Foreign Application Priority Data

Apr. 28, 2005 (JP) ............................. 2005-131751

(51) Int. Cl.
*G01N 21/90* (2006.01)

(52) U.S. Cl. ................. 356/239.5; 250/223 B

(58) Field of Classification Search ................ 356/427, 356/239.6; 250/223 B; 348/127; 209/524
See application file for complete search history.

(56) References Cited

U.S. PATENT DOCUMENTS

| | | | | |
|---|---|---|---|---|
| 4,025,201 A | * | 5/1977 | Deane | 356/239.4 |
| 4,280,624 A | * | 7/1981 | Ford | 356/239.5 |
| 4,500,203 A | * | 2/1985 | Bieringer | 356/239.4 |
| 4,691,231 A | * | 9/1987 | Fitzmorris et al. | 356/239.4 |
| 5,256,871 A | * | 10/1993 | Baldwin | 356/239.4 |
| 6,911,653 B2 | * | 6/2005 | Yagita | 250/341.1 |
| 6,914,672 B2 | * | 7/2005 | Yagita | 356/239.5 |

FOREIGN PATENT DOCUMENTS

| JP | 2001-221746 | 8/2001 |
|---|---|---|
| JP | 2003-315280 | 6/2003 |

* cited by examiner

Primary Examiner—Gregory J. Toatley, Jr.
Assistant Examiner—Juan D Valentin, II
(74) Attorney, Agent, or Firm—Ladas & Parry, LLP

(57) ABSTRACT

An inspecting apparatus for detecting a foreign matter in a container having a recessed and protruding shape includes: illumination units arranged annularly on inner and outer sides of an annular carrier line and casting parallel lights onto the inspection subject from the outside thereof; image pickup units arranged on the outside of the annular carrier line and receiving lights from the inspection subject, simultaneously from two directions around the inspection subject, and picking up images of the inspection subject; wherein the image pickup units pick up images of the inspection subject in a state where an angle θ1 formed by light-receiving axes of the image pickup units is 30 to 90 degrees and an angle θ2 formed by the light-receiving axis of the image pickup unit and the light of the illumination unit next to the image pickup unit is 30 to 60 degrees.

8 Claims, 11 Drawing Sheets

INSPECTING APPARATUS AND METHOD FOR FOREIGN MATTER

BACKGROUND OF THE INVENTION

1. Field of the Invention

This invention relates to an inspecting apparatus and method for a foreign matter (impurities) that enable inspection of all products to detect a foreign matter contained in liquid products (including fluid products) such as beverages and chemicals without stopping a high-speed mass production line, and particularly to an inspecting apparatus and method for a foreign matter that enable secure detection of even a very small foreign matter contained in a liquid product in a container as an inspection subject without making any misjudgment, with the container having a recessed and protruding shape on its lateral side such as a cylindrical container like a PET (polyethylene terephthalate) bottle or a rectangular container like a rectangular bottle and containing a liquid product.

2. Background of the Invention

Recently, as HACCP (Hazard Analysis Critical Control Point System) has been applied to the Food Safety Law and the Product Liability Law has been enforced, it is becoming an obligation to prevent accidents such as microbe contamination that might occur at any stage of manufacturing/processing of products such as foods and chemicals and preservation/circulation of the products before end consumers take them, and contamination by metal, cloth, hair and the like, and to achieve further security of the products.

HACCP is a hazard analysis critical control point system of the United States, which is internationally appreciated as a sanitation control system. This HACCP system is a scientific sanitation control system to achieve safety of products throughout manufacturing processes. Contrary to the conventional sanitation control system, which emphasizes inspection of end products, the HACCP system emphasizes preventive measures in manufacturing processes. The HACCP system consists of two parts, that is, hazard analysis (HA) and critical control point (CCP). The hazard of microbe contamination or the like that might occur at any stage of manufacturing/processing of foods and preservation/circulation of the products before end consumers take them is examined and analyzed, and critical control points for hazard prevention are set. At the same time, control standards are defined so as to check control records to constantly monitor whether appropriate measures are taken within the standards. For other types of hazards, administration and control are based on general sanitation control standards (PP or prerequisite program). Thus, any occurrence of hazard in manufacturing processes is prevented without oversight and further security of products is achieved.

Conventionally, in a mass production line at a manufacturing plant, visual inspection by workers or the like is carried out to detect a foreign matter contained in a liquid after filling a container with it. Since such visual inspection takes time and labor, sampling inspection to select one of every given number of containers for inspection is carried out. Therefore, there is a problem that this is not a secure inspection technique for all the products.

In a complete inspection system where inspectors are stationed in the production line, though relatively large foreign matters can be detected by visual judgment by the workers, there is a problem that very small foreign matters cannot be detected, resulting in low detection accuracy. Moreover, practically, the visual judgment capability of the inspectors cannot catch up with the increasingly higher speed of the production line, resulting in low inspection efficiency.

As a technique for detecting a foreign matter contained in a container after it is filled with a liquid without using visual inspection, a technique of photographing a container from outside by an inspection camera and then detecting the existence of any defect based on the acquired image information is considered.

FIG. 1 shows one example of this. A container 101 moving without having any spacing into the direction of an arrow X on a production line is used as an inspection subject. The container 101 is illuminated from its lateral side by a light source 100. Transmitted light from the container 101 is received by a CCD sensor 102, which is an image pickup unit. A light-receiving signal from the CCD sensor 102 is image-processed by a data processing device (not shown). A foreign matter contained in a liquid product in the container 101 (foreign matter 103 in FIG. 1 or the like) is thus detected. In such an inspecting apparatus, the CCD sensor 102 receives the transmitted light from the container 101 and the light-receiving signal from the CCD sensor 102 is processed by an image processing device such as a personal computer. A foreign matter contained in the liquid product in the container 101 is thus detected (see, for example, Patent Reference 1).

Patent Reference 1: JP-A-2001-221746

Patent Reference 2: JP-A-2003-315280

In the inspecting apparatus as described above, there is no problem with a container having a simple shape and having no recess and protrusion on its surface. However, in the case of a container having a recessed and protruding shape on its lateral side such as a rectangular bottle or PET bottle, the recessed and protruding shape appears on its picked-up image, making it difficult to detect a foreign matter. That is, since reflection on the container surface of scattered light from outside and problems on the emission line are caused by the diverse and complicated container shapes and materials, the recess and protrusion on the container surface and the contour of the container cause changes in luminance similar to those caused by foreign matters and image information (raw data) as shown in FIG. 2 is acquired by the CCD sensor 102. Therefore, even when the image information is processed by the image processing device and a binary image as shown in FIG. 3 is acquired, it is difficult to accurately discriminate only a foreign matter on the image. In short, in addition to lowering of reliability, there is a problem of deterioration in manufacturing yield because a foreign matter and an irregular reflection part of the container cannot be discriminated from each other, resulting in detection error.

In consideration of the above-described problems, which occur when a container having a recessed and protruding shape is used as a subject, for example, an inspecting apparatus for foreign matter disclosed in Patent Reference 2 by the present applicant is provided. For example, when this inspecting apparatus for foreign matter is applied to a production line, light is cast onto an inspection subject 101, which is a container moving on the production line into the direction of an arrow X and contains a liquid product, from a first lateral side by a light source 100A, and light is cast onto the inspection subject 101 by two light sources 100B, 100C from two inclined directions on a second lateral side opposite to the first lateral side (at an inclination angle of 30 to 60 degrees to a perpendicular line to the subject inspection on the first lateral side), as shown in FIG. 4. Then, an image pickup unit (CCD sensor) 102 near the second lateral side receives transmitted light and reflected light from the inspection subject 101. On the basis of an image signal from the image pickup unit 102, a foreign matter contained in the liquid product (foreign matter 103 in FIG. 4 or the like) is detected (see Patent Reference 2).

In such an inspection technique, the outer shape line of the inspection subject 101 (PET bottle or the like) is eliminated from the image captured by the image pickup unit 102, thus enabling highly accurate detection of a foreign matter contained in the liquid product. However, in the case of the optical inspection for a foreign matter on a straight line as in the inspecting apparatus described in Patent Reference 2, there is a problem that a blind spot is generated when light is transmitted. If a recessed and protruding shape exists or a foreign matter exists in the blind spot, it is difficult to discriminate the foreign matter from the recessed and protruding part, and a misjudgment may occur. For example, in the arrangement of the optical system as shown in FIG. 4, if the inclination angle is 45 degrees and a PET bottle having large recesses and protrusions is a subject, the CCD sensor 102 may acquire image information (raw data) as shown in FIG. 5, depending on the direction of the PET bottle. Therefore, even when the image information is processed by the image processing device to acquire a binary image as shown in FIG. 3, a part of the recesses and protrusions of the container and the contour of the container cannot be totally optically eliminated, and in some cases, it is not possible to accurately discriminate only the foreign matter on the image. Also, in the optical inspection for a foreign matter on a straight line as in the inspecting apparatuses described in Patent Reference 1 and Patent Reference 2, even when the arrangement of the optical system is advantageously contrived, the linear carrier path may become a barrier. When inspecting the container 101 carried along with the other containers in a chained manner as shown in FIG. 1, the adjacent containers may become obstacles. Therefore, it is not possible to completely eliminate the blind spot.

As another inspection technique, a technique of performing image editing based on software after capturing an image and thus masking unwanted parts outside of the inspection area such as the shape line of the container may be considered. However, usually, products with various rotation angles move into the image pickup area of the inspecting apparatus installed on the production line. Therefore, when images of the containers are captured, the position of the recess and protrusion on the surface of the container differs each time, thus causing a problem that it is impossible to fixedly set the masking area.

SUMMARY OF THE INVENTION

In view of the foregoing status of the art, it is an object of this invention to provide an inspecting apparatus and method for a foreign matter that enable secure and high-speed detection of a foreign matter contained in a liquid product in a container without stopping a production line, even when a cylindrical container such as a PET bottle having a recessed and protruding shape on its lateral side or a rectangular container such as a rectangular bottle is an inspection subject.

This invention relates to an inspecting apparatus and method for a foreign matter in which a container such as a PET bottle or rectangular bottle having a recessed and protruding shape on its lateral side and containing a liquid product is an inspection subject, the inspection subject being sequentially set upright in each setting part provided on the circumference of a star wheel that is rotationally driven in synchronization with carrier speed on a production line, the inspection subject being inspected for any foreign matter in the liquid product while it is carried at a high speed along an annular line in the form of coaxial and equal-speed rotation with the star wheel. The foregoing object of this invention is achieved by the inspecting apparatus for a foreign matter including: a plurality of illumination units that are arranged annularly on inner and outer sides of the annular carrier line having the setting part provided on its circumference, to surround the lateral side of the inspection subject, and that cast a luminous flux substantially perpendicular to a vertical cross section of the inspection subject and including parallel rays, as illumination light, onto the lateral side of the inspection subject from a plurality of directions around the inspection subject; first and second image pickup units that are arranged on the outer side of the annular carrier line and that simultaneously receive transmitted light and reflected light from the inspection subject illuminated by the illumination units, from two directions around the inspection subject, and respectively pick up images of the lateral side of the inspection subject; and an inspection unit that inspects the existence of a foreign matter contained in the liquid product on the basis of image signals of the first and second image pickup units; wherein the first and second image pickup units respectively pick up images of the inspection subject in a state where an angle θ1 formed by light-receiving axes of the first and second image pickup units is 30 to 90 degrees and an angle θ2 formed by the light-receiving axis of the image pickup unit and the luminous flux of the illumination unit next to the image pickup unit is 30 to 60 degrees.

Moreover, the foregoing object of this invention is achieved more effectively by the following features: the illumination unit arranged on the outer side of the annular carrier line includes a first illumination unit situated at a central part between the first and second image pickup units, a second illumination unit situated at a position opposite to the first illumination unit with respect to the first image pickup unit between them, and a third illumination unit situated at a position opposite to the first illumination unit with respect to the second image pickup unit between them; the angle θ1 is substantially 90 degrees; when an angle formed by the light-receiving axis of the first image pickup unit and a luminous flux of the second illumination unit is θ2a and an angle formed by the light-receiving axis of the second image pickup unit and a luminous flux of the third illumination unit is θ2b, θ2a=θ2b holds, which is equal to substantially 45/2 degrees; the illumination unit arranged on the inner side of the annular carrier line includes a first illumination unit arranged to face the first image pickup unit and a second illumination unit arranged to face the second image pickup unit; and the setting part is formed by a translucent member, and an illumination unit is further provided that casts a luminous flux including parallel rays perpendicularly to a bottom side of the inspection subject from below the setting part.

The foregoing object of this invention is also achieved by the inspection method for foreign matter including the steps of: casting a luminous flux substantially perpendicular to a vertical cross section of the inspection subject and including parallel rays, as illumination light, onto the lateral side of the inspection subject from a plurality of directions around the inspection subject by a plurality of illumination units that are arranged annularly on inner and outer sides of the annular carrier line to surround the lateral side of the inspection subject; simultaneously receiving transmitted light and reflected light from the inspection subject illuminated by the illumination units, from two directions around the inspection subject, and picking up images of the lateral side of the inspection subject by first and second image pickup units that are arranged on the outer side of the annular carrier line, in a state where an angle θ1 formed by light-receiving axes of the first and second image pickup units is 30 to 90 degrees and an angle θ2 formed by the light-receiving axis of the image pickup unit and the luminous flux of the illumination unit next to the image pickup unit is 30 to 60 degrees; and inspecting the existence of a foreign matter contained in the liquid product on the basis of image signals from the first and second image pickup units.

DETAILED DESCRIPTION OF THE PREFERRED EMBODIMENTS

Figure 1:
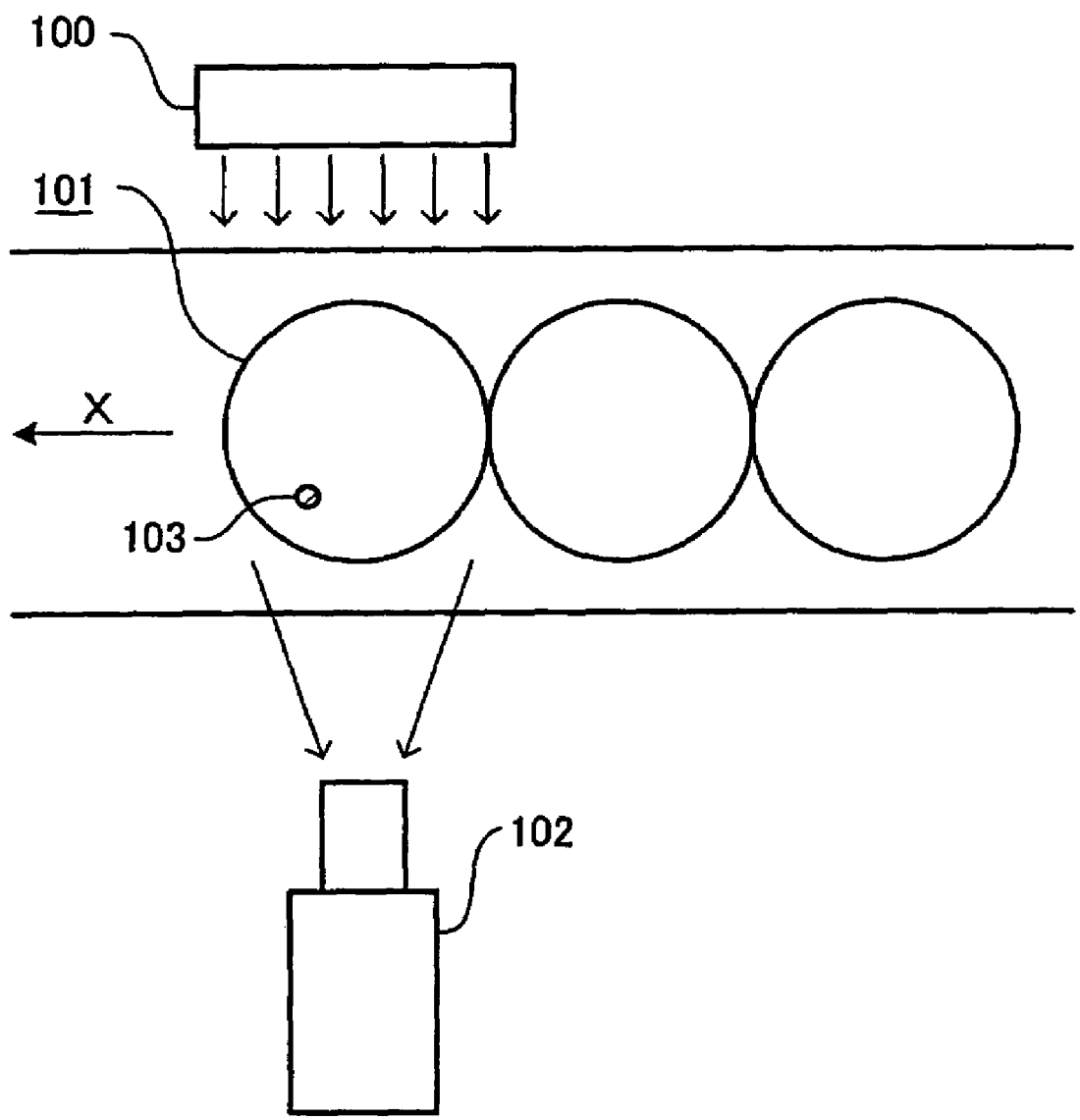
FIG. 1 is a structural view showing a first example of conventional inspecting apparatus for a foreign matter.
Figure 2:
FIG. 2 shows a photographic image of an exemplary picked-up image (raw data) by the inspecting apparatus for a foreign matter of FIG. 1.
Figure 3:
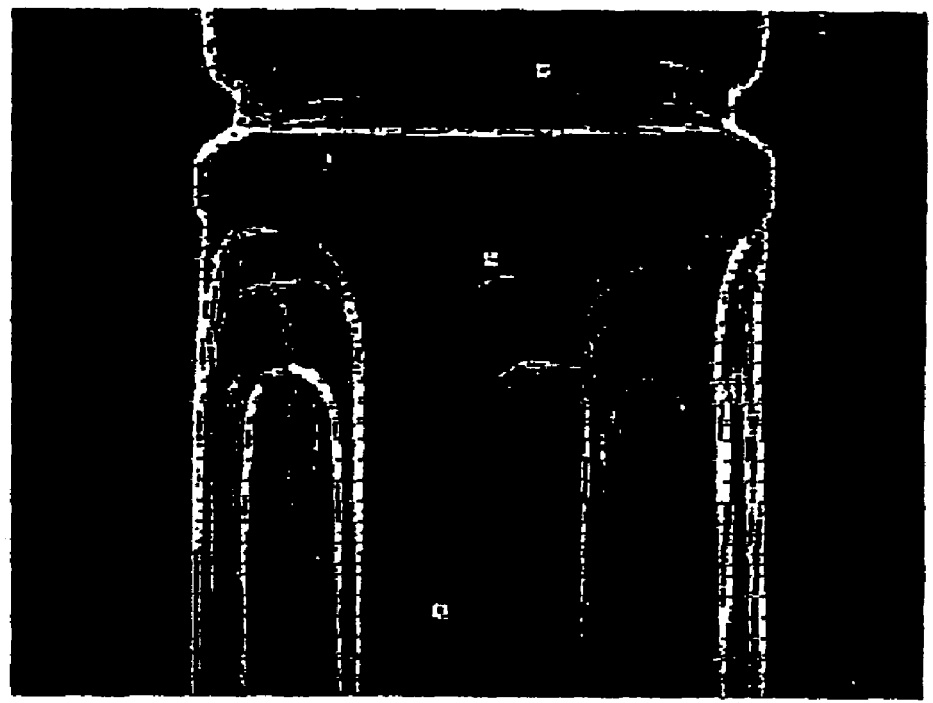
FIG. 3 shows an image produced by binarizing the picked-up image of FIG. 2.

An inspecting apparatus for a foreign matter according to this invention is adapted for performing secure and high-speed inspection to detect whether a foreign matter is contained in a liquid product in an inspection subject that is being carried at a high speed by a rotary carrier unit, wherein inspection targets to be detected include foreign matters generated in manufacturing/processing processes of a product, material foreign matters that have not been completely removed by material inspection, ambient foreign matters that can enter when a production line is started, and machine foreign matter that may be generated from a manufacturing machine itself during the production, and wherein inspection subjects include containers containing liquid products (including fluid products) such as beverages and chemicals, particularly containers having recessed and protruding shapes on their lateral sides such as a cylindrical container like PET bottle or a rectangular container such as rectangular bottle.

In this invention, the problems with the conventional optical inspection technique for a foreign matter on a straight line are solved. Contaminants contained in the liquid product (floating foreign matter, foreign matter in the liquid, and deposited foreign matter) are securely detected at the final stage and detection errors are prevented. Therefore, in this invention, an optical inspection technique for a foreign matter on an annular line (annular carrier line) is employed, and the position of each illumination unit, its light casting direction, the positions of image pickup units and the viewing directions of their viewpoints are contrived so as to prevent occurrence of a blind spot in the light casting area to the inspection subject and the fields of view of the image pickup units. Thus, when the image pickup units captures the inspection subjects from their viewing directions, no matter which direction the carried inspection subject faces having recessed and protruding shape on its lateral side, an image that clearly shows only a foreign matter is formed by eliminating the recessed and protruding shape of the container and its contour part almost perfectly from the image. By causing such an optical phenomenon to occur, even for a container having a complicated shape or a container having large recesses and protrusions, it is possible to securely discriminate only a foreign matter contained in a liquid filling the container from luminance changes generated by the container itself, without being affected by reflection of external scattered light and occurrence of emission lines. Also, image processing of the foreign matter captured by the image pickup units is facilitated. Moreover, in this invention, since the lateral side of the inspection subject is captured simultaneously from two directions, foreign matters in the liquid products can be securely detected, including foreign matters at both ends on the front side of the container, which tend to become blind spots from the viewpoints of the image pickup units, and glass pieces and thin film-like foreign matters that are hard to capture depending on the viewing direction.

Hereinafter, a preferred embodiment of this invention will be described in detail with reference to the drawings.

Figure 7:
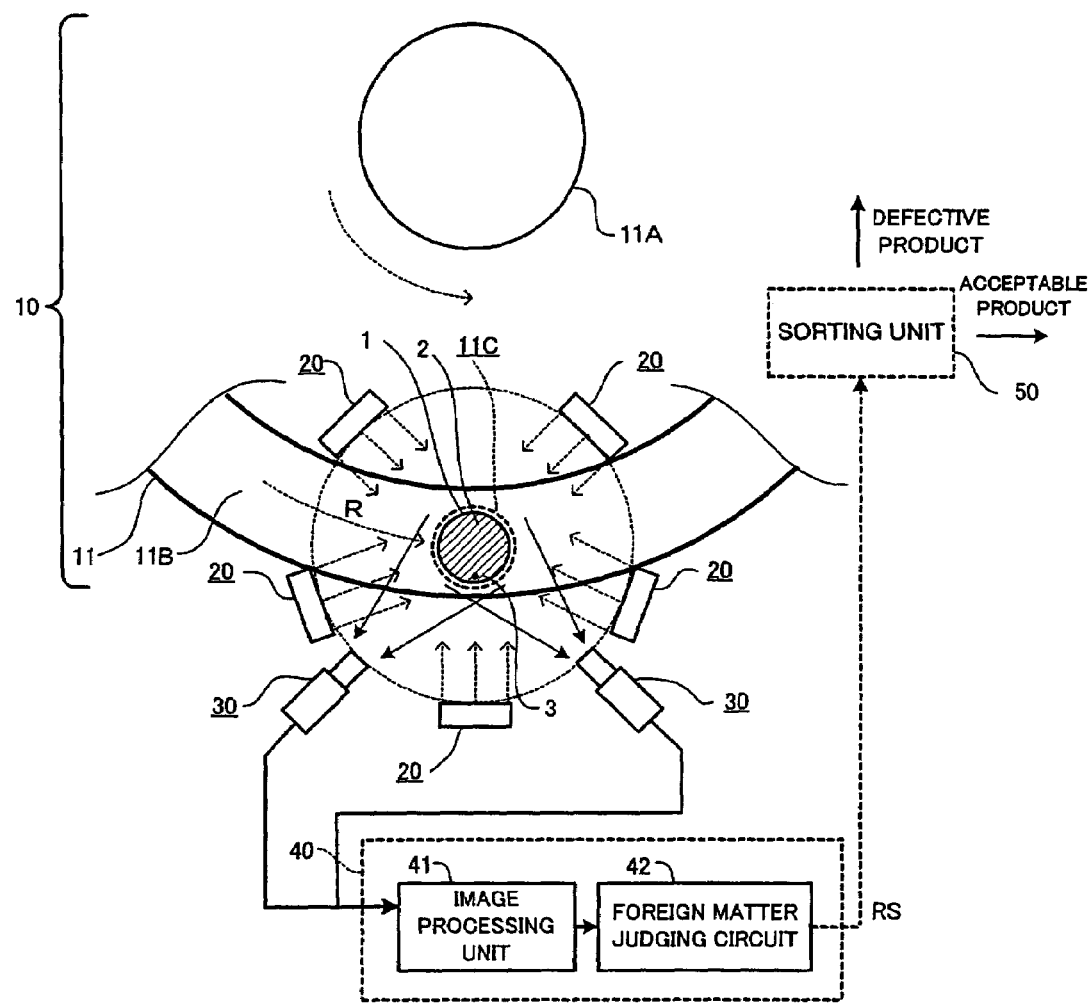
FIG. 7 is a schematic structural view showing an example of inspecting apparatus for a foreign matter according to this invention.
Figure 8:
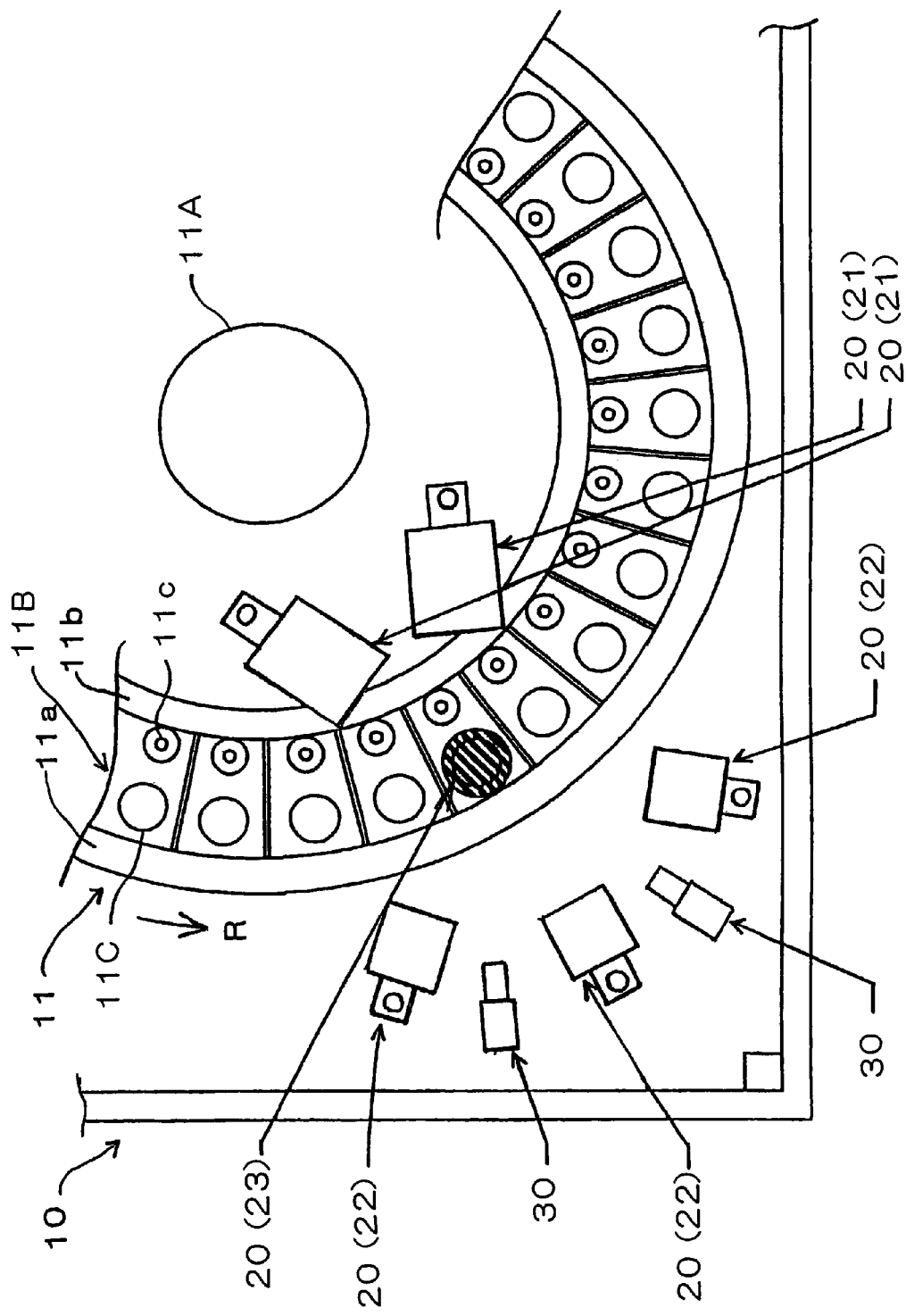
FIG. 8 is a plan view showing an exemplary structure of an annular carrier line of the inspecting apparatus for a foreign matter according to this invention and an exemplary arrangement of illumination devices and image pickup cameras.

FIG. 7 is a schematic structural view showing an example of an inspecting apparatus for a foreign matter according to this invention. FIG. 8 is a plan view showing an exemplary structure of an annular carrier line installed on an inspection stage and an exemplary arrangement of illumination devices and image pickup cameras. First, a mode of carrying an inspection subject according to this invention will be described. An inspection subject (for example, PET bottle or glass bottle) containing a liquid product on a production line is continuously carried to an inspection stage, for example, by a carrier conveyer that shifts linearly. On the inspection stage, an inspection table (large-diameter star wheel) 11 that is rotationally driven about a rotary shaft 11A in synchronization with the carrier speed on the production line is provided as a rotary carrier unit 10. The inspection subject brought to the inspection stage is sequentially set upright on a setting part 11C provided on the circumference of the inspection table 11 (hereinafter referred to as "star wheel") and is carried along an annular line indicated by an arrow R in FIG. 7. In the inspecting apparatus for a foreign matter according to this invention, all the inspection subjects that are being carried at a high speed (for example, approximately 1000 bottles per minute) in the form of coaxial and equal-speed rotation with the star wheel 11 are inspected in real time so as to detect whether a foreign matter is contained in the liquid products in the containers.

Figure 9:
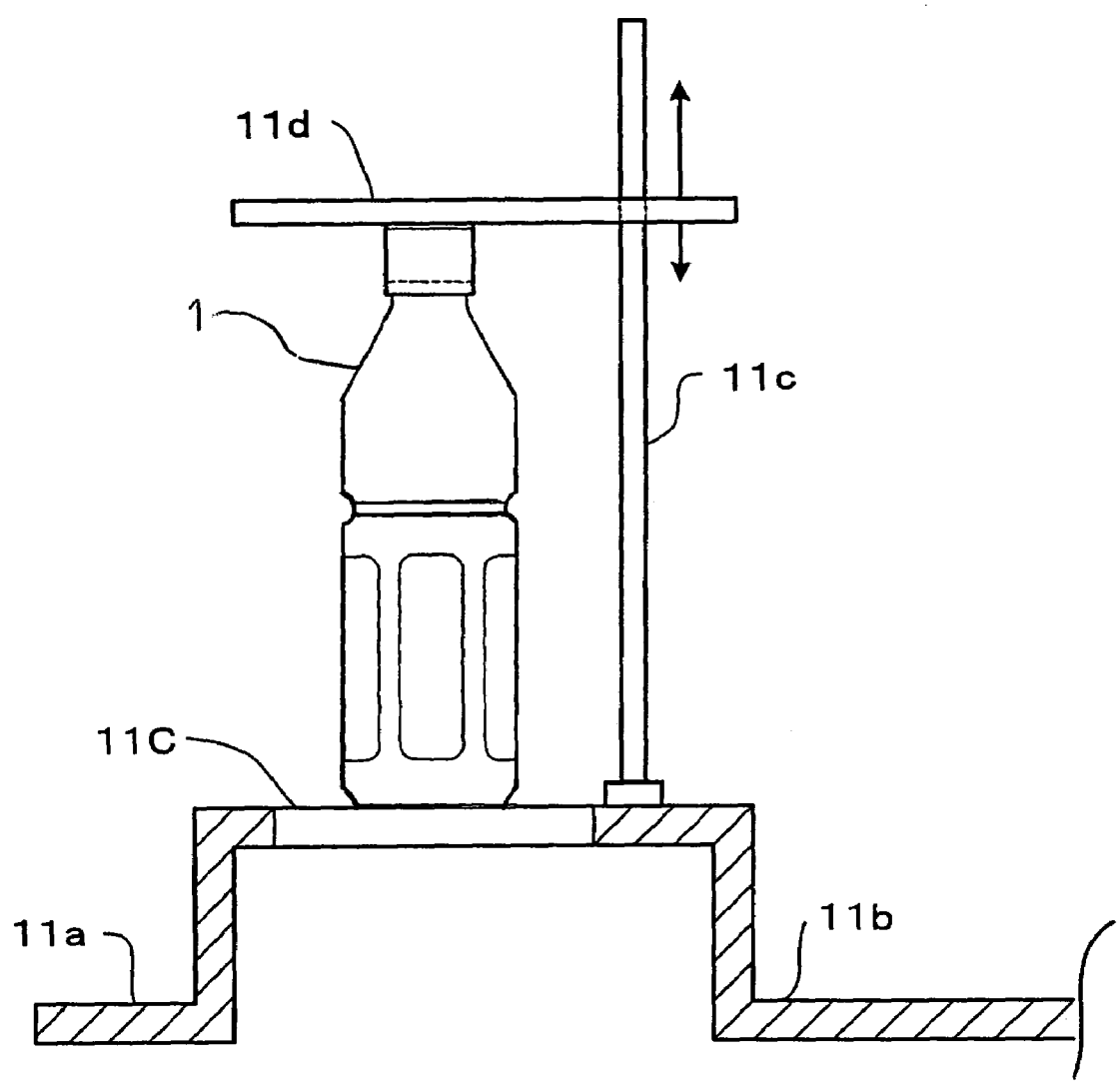
FIG. 9 is a side view (partial sectional view) showing an exemplary shape of a container as an inspection subject and the setting state of the inspection subject on the annular carrier line in this invention.

The setting part 11Cs for setting the inspection subjects thereon are provided annularly at equal spacing on the star wheel 11, as shown in FIG. 8. Beside each setting part 11C on the annular carrier line 11B, a tight holding unit that tightly holds the inspection subject 1 by pressing the top of the inspection subject 1 with a top plate 11d made of a translucent member (translucent member functioning also as an optical filter to prevent irregular reflection) is provided, as shown in FIG. 9. The part denoted by a numeral 11c in FIG. 8 represents a supporting shaft 11c (made of a translucent member) of the top plate 11d. In this example, at the timing when the inspection subject is carried to the inspection stage and set on the setting part 11C on the annular carrier line, the top plate 11d is lowered by rotation of an eccentric cam (the top plate falls by its own weight or is moved downward by a spring or the like) and the inspection subject 1 is fixed on the setting part 11C. When carrying the inspection subject 1 out, the top plate 11d is raised to release the inspection subject 1 and the inspection subject 1 is carried onto the carrier conveyor on the production via the carrier line on the carry-out star wheel. The inspection table (star wheel) 11 is a table of two-stage structure in which the parts 11a, 11b on both sides of the setting part 11C are formed to be lower than the setting part 11C, as shown in FIG. 9. In this embodiment, the lower parts of light-emitting surfaces of illumination devices 20 and the lower parts of light-receiving surfaces of image pickup cameras 30 are arranged at positions lower than the setting part 11C, thus preventing occurrence of blind spots with respect to the bottom side of the inspection subject 1.

Next, the overall structure of the inspecting apparatus for a foreign matter will be described.

In the exemplary structure of FIG. 7, the inspecting apparatus for a foreign matter has: a rotary carrier unit (carrying means) 10 including a carry-in/carry-out star wheel connected to the carrier conveyor on the production line, the above-described star wheel 11 for inspection and the like; plural illumination units (illuminating means) 20 that cast parallel light to the lateral part of the inspection subject 1 being carried at a high speed by the carrier unit 10, from plural directions around the inspection subject 1; plural image pickup units (imaging means) 30 that pick up images of the lateral part of the inspection subject 1 illuminated by each illumination unit 20, at different azimuth angles; and an inspection unit (inspecting means) 40 that inspects the existence of a foreign matter contained in the liquid product in real time on the basis of an image signal from each image pickup unit 30.

The illumination units 20 are arranged annularly on the inner and outer sides of the annular carrier line 11B having the setting parts 11C provided on its circumference, to surround the lateral part of the inspection subject 1. The illumination units 20 cast luminous fluxes substantially perpendicular to the vertical cross section of the inspection subject 1 and including parallel rays, as illumination light, to the lateral part of the inspection subject 1 from plural directions around the inspection subject 1. As for the number of illumination devices used as the illumination units 20, in the example of FIG. 8, two illumination devices 21 as transmitted light illumination units on the inner side of the annular carrier line 11B and three illumination devices 22 as reflected light illumination units on the outer side of the annular carrier line 11B are provided, that is, five illumination devices in total. For these illumination units 20, the directions of the luminous fluxes (illuminating directions of parallel rays) cast onto the lateral part of the inspection subject 1, and the angles formed by the luminous fluxes and the light-receiving axis of the image pickup units are important. The specific illuminating direction of each illumination unit 20 will be described later.

The image pickup units 30 are formed by image pickup cameras including CCDs (charge-coupled devices) and are arranged on the outer side of the annular carrier line 11B. The image pickup units 30 receive transmitted light and reflected light from the inspection subject 1 illuminated by the illumination units 20, from plural directions around the inspection subject 1 (in this example, two directions), and simultaneously pick up images of the lateral part of the inspection subject 1 from the respective directions. The main purpose of installing the image pickup units 30 on the outer side of the annular carrier line 11B is to capture a foreign matter 3 from the vicinity of the viewpoints of the image pickup cameras 30 when the foreign matter 3 in the liquid product 2 is moved to the wall of the container or the end part of the bottom of the container (toward the image pickup cameras), which is on the outer part of the annular carrier line 11B, by a centrifugal force due to high-speed rotation of the star wheel 1, as shown in FIG. 7. In the schematic view of FIG. 7, the light-emitting surfaces of the illumination units 20 and the image pickup surfaces of the image pickup units 30 are arranged on the same circumference. However, they need not be arranged on the same circumference and the image pickup units 30 are provided more closely to the annular carrier line 11B in accordance with their fields of view and the like.

The image pickup units 30 (and the illumination units 20) are axially supported so that they can freely rise and fall vertically and can freely rotate horizontally. The image pickup units 30 (and the illumination units 20) are also axially supported so that their angles in the horizontal and vertical directions are adjustable. As for the image pickup cameras used as the image pickup units 30, plural image pickup cameras can be arranged vertically and plural image pickup cameras can be arranged horizontally. Depending on the inspection area, one or plural image pickup cameras are arranged. These image pickup cameras have their positions and directions adjusted in accordance with the height and shape of the inspection subject, and the cameras to be used (for example, the cameras on the second and fourth stages in each line) are selected, for example, by manual operation or by control from an external device. In the foreign matter inspection process from the lateral side of the inspection subject according to this invention, for example, two image pickup cameras adjusted to have the positions and azimuth angles shown in FIG. 7 are installed. The purpose of picking up images of the inspection subject from the two directions around the inspection subject by the two image pickup units 30 is to prevent occurrence of blind spots on both ends on the front side of the container with respect to the viewing directions of the image pickup units 30 and to enable secure detection of glass pieces and thin film-like foreign matters, which are hard to capture depending on the viewing direction.

The inspection unit 40 has an image processing unit 41 that performs image processing of picked-up image signals, and a foreign matter judging circuit 42 for judging the existence of a foreign matter in accordance with the image processing, as shown in FIG. 7. The inspection unit 40, to which image signals picked up by the image pickup signals 30 have been inputted, for example, differentiates the analog image signal, compares the differentiated image signal with a predetermined threshold, and then compares a signal level obtained by emphasizing a part with a large quantity of change of the differentiated value, that is, a part where the output level changes abruptly, with a reference level (or compares a total value of binarized pixel values within the inspection area with a reference value), thus inspecting the existence of a foreign matter in the container (particularly a foreign matter in the liquid product). The foreign matter judging circuit 42 outputs a removal signal RS when it is judged that there is a foreign matter. A sorting unit 50 for the inspection subjects is provided on the production line. The inspection subjects corresponding to the removal signal RS are classified into acceptable products and defective products by the sorting unit 50, and the defective products are removed from the production line. This enables production and shipment of acceptable products only.

Next, the arrangement and illuminating directions of the illumination units 20, and the arrangement and image pickup directions of the image pickup units 30 will be described in detail with reference to the drawings.

Figure 10:
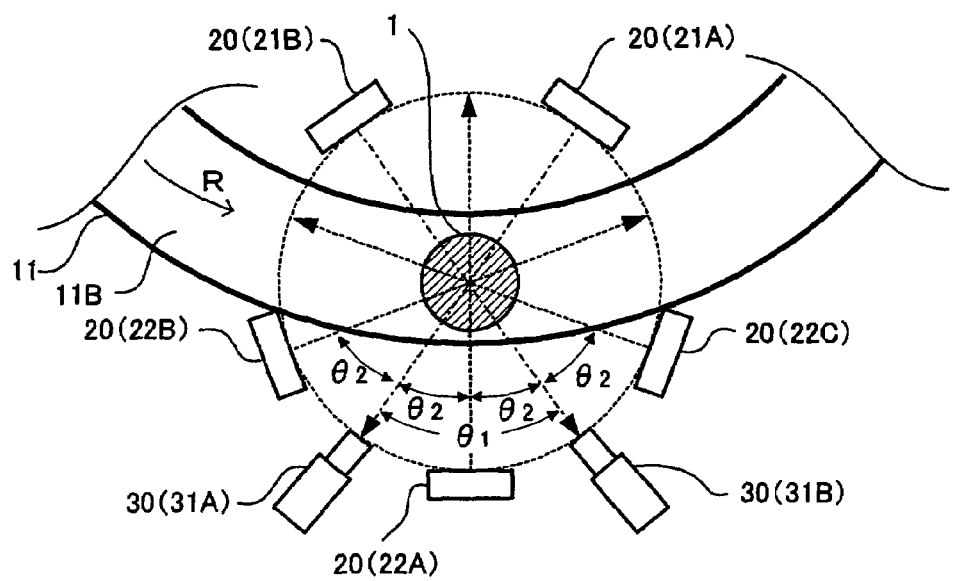
FIG. 10 is a plan view showing a first example of arrangement of illumination units and image pickup units in this invention.

FIG. 10 is a plan view showing a first exemplary arrangement of the illumination units (light sources) and the image pickup units (image pickup cameras). In this example, five illumination units 20 are arranged at substantially equal spacing on the circumference of a circle about the center of the inspection subject 1 on the annular carrier line 11B. In this case, two illumination units 20 (21A, 21B) are arranged on the inner side of the annular carrier line 11B, and three illumination units 20 (22A, 22B, 22C) are arranged on the outer side of the annular carrier line 11B. The light sources of these illumination units 20 have the same quantity of light. In this example, the five illumination units 20 are arranged at substantially equal spacing. However, if the angle formed by the light-receiving axis of the image pickup unit 30 (31A, 31B) and the luminous flux of the illumination unit 20 (22B/22A, 22A/22C) next to that image pickup unit 30 (31A, 31B) is $\theta 2$, the direction of casting illumination light of the respective illumination units 20 (22A, 22B, 22C) may be arranged within such a range that the angle $\theta 2$ is 30 to 60 degrees. In addition, the illumination units 20 (transmitted light illumination units 21A, 21B) on the inner side of the annular carrier line 11B is not particularly limited as long as they can uniformly illuminate the lateral part of the inspection subject 1. In this example, these illumination units are arranged to face the image pickup units 31A, 31B.

Meanwhile, as the image pickup units 30, two image pickup units (image pickup cameras) 31A, 31B are arranged on the outer side of the annular carrier line 11B. If the angle formed by the light-receiving axes of these image pickup units 31A, 31B is $\theta 1$, the direction of image pickup of the image pickup units 31A, 31B may be set within such a range that the angle $\theta 1$ is 30 to 90 degrees. In this example, the image pickup unit 31A is arranged at the center between the illumination unit 22A and the illumination unit 22B, and the image pickup unit 31B is arranged at the center between the illumination unit 22A and the illumination unit 22C.

As parallel light is thus cast as illumination light onto the lateral part of the inspection subject from the plural directions around the inspections subject, the parallel light becomes incident on the recessed and protruding part of the lateral part of the inspection subject 1 at various angles, and the inside of the liquid is filled with uniform light. Since the transmitted light and reflected light from the inspection subject 1 are simultaneously received in this state, the outer shape line of the lateral part of the inspection subject (the part of the recessed and protruding shape and the contour of the container), and the liquid surface, which is usually captured as a black contour line, are optically eliminated from the images captured by the image pickup units 31A, 31B. Therefore, an image of a foreign matter alone can be acquired and even a foreign matter in the liquid or a floating foreign matter existing on the outer shape line can be securely detected. The setting part 11C on the annular carrier line 11B shown in FIG. 8 is formed by a translucent member (hard glass filter or the like) that also functions as an optical filter for preventing irregular reflection. In this embodiment, below the setting part 11C, a perpendicular illumination unit (illumination unit 23 in FIG. 8) that casts a luminous flux including parallel rays perpendicularly to the bottom of the inspection subject 1 is installed as an additional constituent element. As such an illumination unit is provided, the inside of the sidewall of the container and the inside of the liquid are further filled with uniform light.

Figure 11:
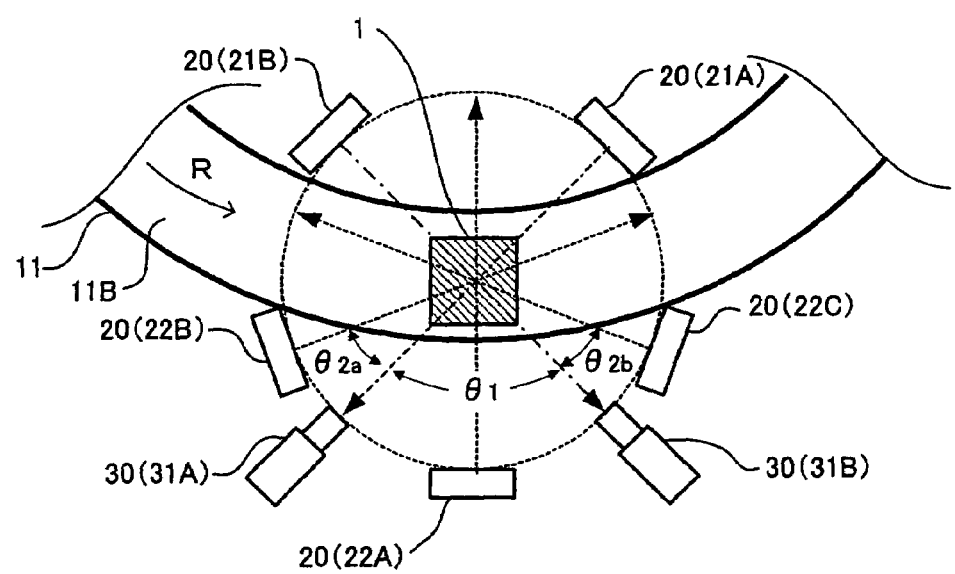
FIG. 11 is a plan view showing a second example of arrangement of illumination units and image pickup units in this invention.
Figure 12:
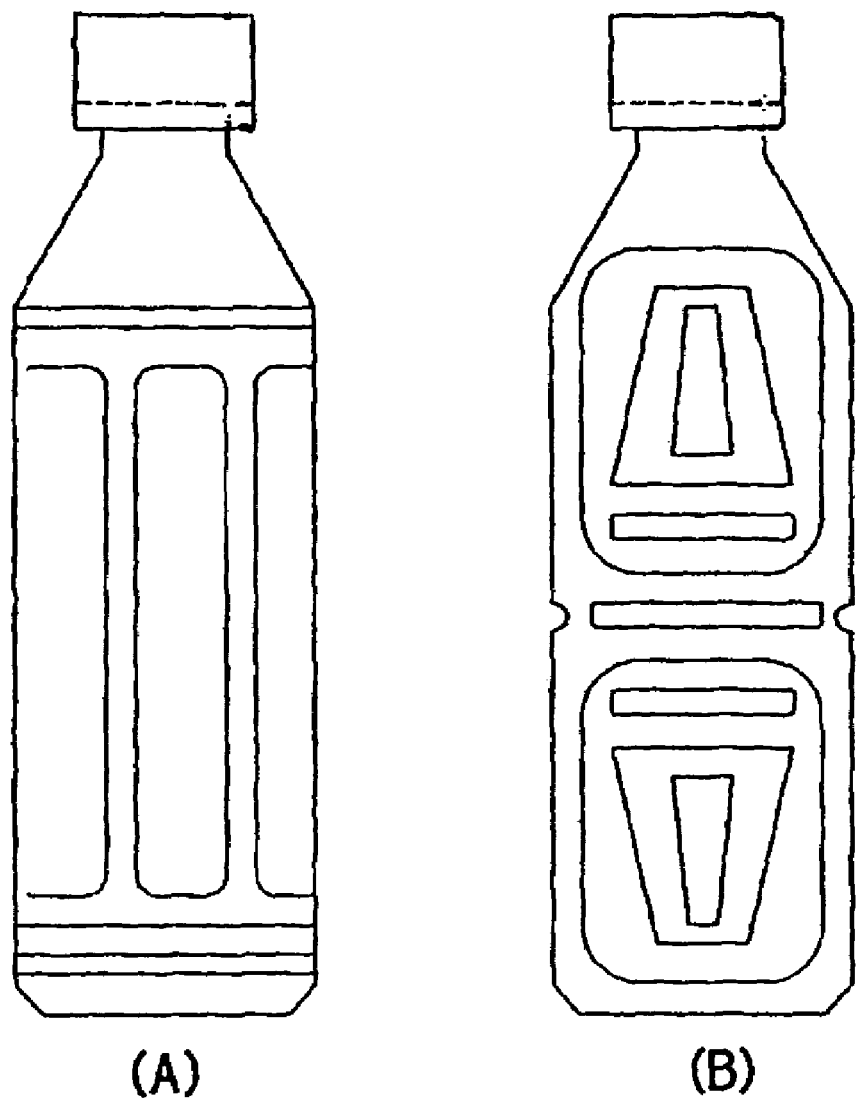
FIGS. 12A and 12B are side views showing other exemplary shapes of a container as an inspection subject.

FIG. 11 shows a second exemplary arrangement of the illumination units and the image pickup units. This example shows an optical arrangement of the illumination units 20 and the image pickup units 30. As inspection subjects containing a liquid product, rectangular containers such as a rectangular bottle may be used other than cylindrical containers such as PET bottles. In the case of PET bottles, there are containers having complicated shapes such as PET bottles having shapes as shown in FIGS. 12A and 12B, in addition to the PET bottle having the shape as shown in FIG. 9. On the contrary, in the case of a rectangular bottle, though the shape of the container is not complicated, there are edge parts where planes cross each other. If a foreign matter exists on or near the edge, it is difficult to detect the foreign matter. While such a foreign matter can be detected by using the arrangement shown in FIG. 10, the arrangement shown in FIG. 11 is the best in the case of using containers of various shapes including PET bottles and rectangular bottles as inspection subjects.

In this example, the image pickup units 31A, 31B are arranged so that the angle $\theta 1$ formed by the light-receiving axes of these image pickup units is substantially 90 degrees. Of the illumination units 22A, 22B, 22C arranged on the outer side of the annular carrier line 11B, the illumination unit 22A is arranged at the center between the image pickup units 31A, 31B, and the illumination units 22B, 22C are arranged so that if the angle formed by the light-receiving axis of the image pickup unit 31A and the luminous flux of the illumination unit 22B is $\theta 2a$ and the angle formed by the light-receiving axis of the image pickup unit 31B and the luminous flux of the illumination unit 22C is $\theta 2b$, $\theta 2a=\theta 2b$ holds, which is equal to substantially 45/2 degrees. With such an arrangement, since an image of the rectangular bottle 1 is formed from which its edge parts have been eliminated almost perfectly, a misjudgment to judge the edge parts as foreign matters can be avoided. Moreover, even when a very small foreign matter exists on the edge part (contour) of the rectangular bottle 1, the foreign matter can be securely detected. Similarly, even for a cylindrical bottle such as a PET bottle, a foreign matter can be securely detected without making any misjudgment, irrespective of the position of the existing foreign matter and the type of recessed and protruding shape.

Figure 13:
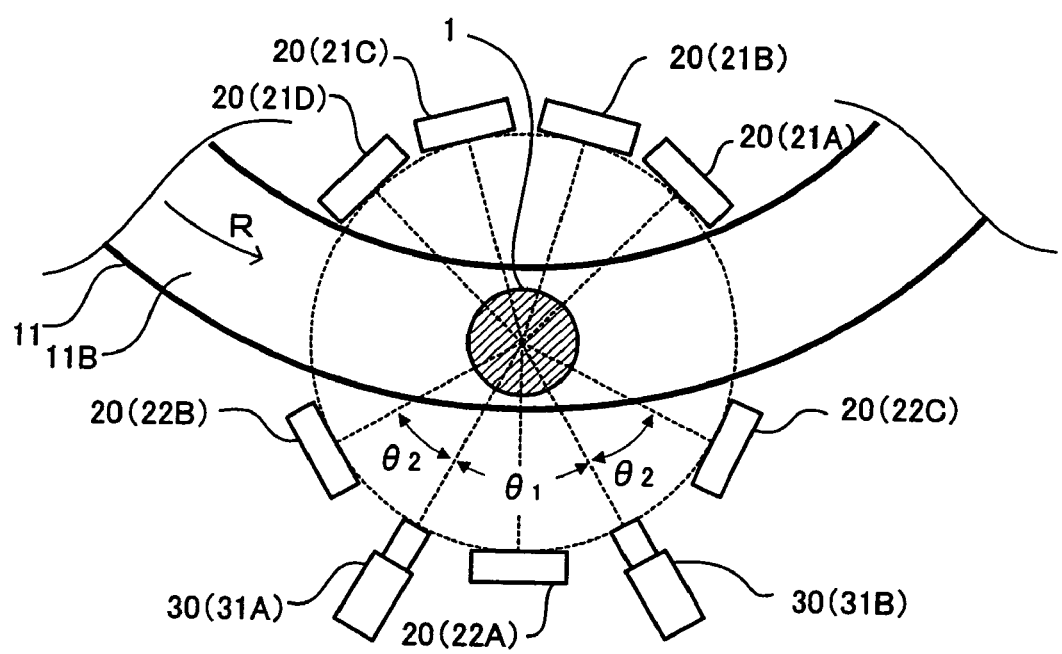
FIG. 13 is a plan view showing a third example of arrangement of illumination units and image pickup units in this invention.

FIG. 13 shows a third exemplary arrangement of the illumination units and the image pickup units. This example differs from the first and second examples in that the angle θ1 formed by the light-receiving axes of the image pickup units 31A, 31B is an acute angle, that four illumination units 21A, 21B, 21C, 21D are arranged on the inner side of the annular carrier line 11B, and that the image pickup units 31A, 31B are arranged not to face the illumination units on the inner side of the annular carrier line 11B. Even with such an arrangement, the part of the recessed and protruding shape formed on the lateral part of the inspection subject 1 and the contour of the container can be optically eliminated from the images captured by the image pickup units 31A, 31B, and an image of a foreign matter only can be acquired.

As described above, in this invention, plural illumination units are arranged on the inner and outer sides of an annular carrier line to surround the lateral part of an inspection subject, and luminous fluxes substantially perpendicular to a vertical cross section of the inspection subject being carried at a high speed along the annular line and including parallel rays are cast as illumination light onto the lateral part of the inspection subject from plural directions around the inspection subject. Two image pickup units arranged on the outer side of the annular carrier line receive transmitted light and reflected light from the inspection subject illuminated by the plural illumination units, simultaneously from two directions around the inspection subject, in a state where an angle θ1 formed by the light-receiving axes of the two image pickup units is 30 to 90 degrees and an angle θ2 formed by the light-receiving axis of the image pickup unit and the luminous flux of the illumination unit next to that image pickup unit is 30 to 60 degrees. The two image pickup units thus pick up images of the lateral part of the inspection subject. On the basis of image signals from these image pickup units, the existence of a foreign matter contained in a liquid product in the container, which is the inspection subject, is inspected.

Figure 4:
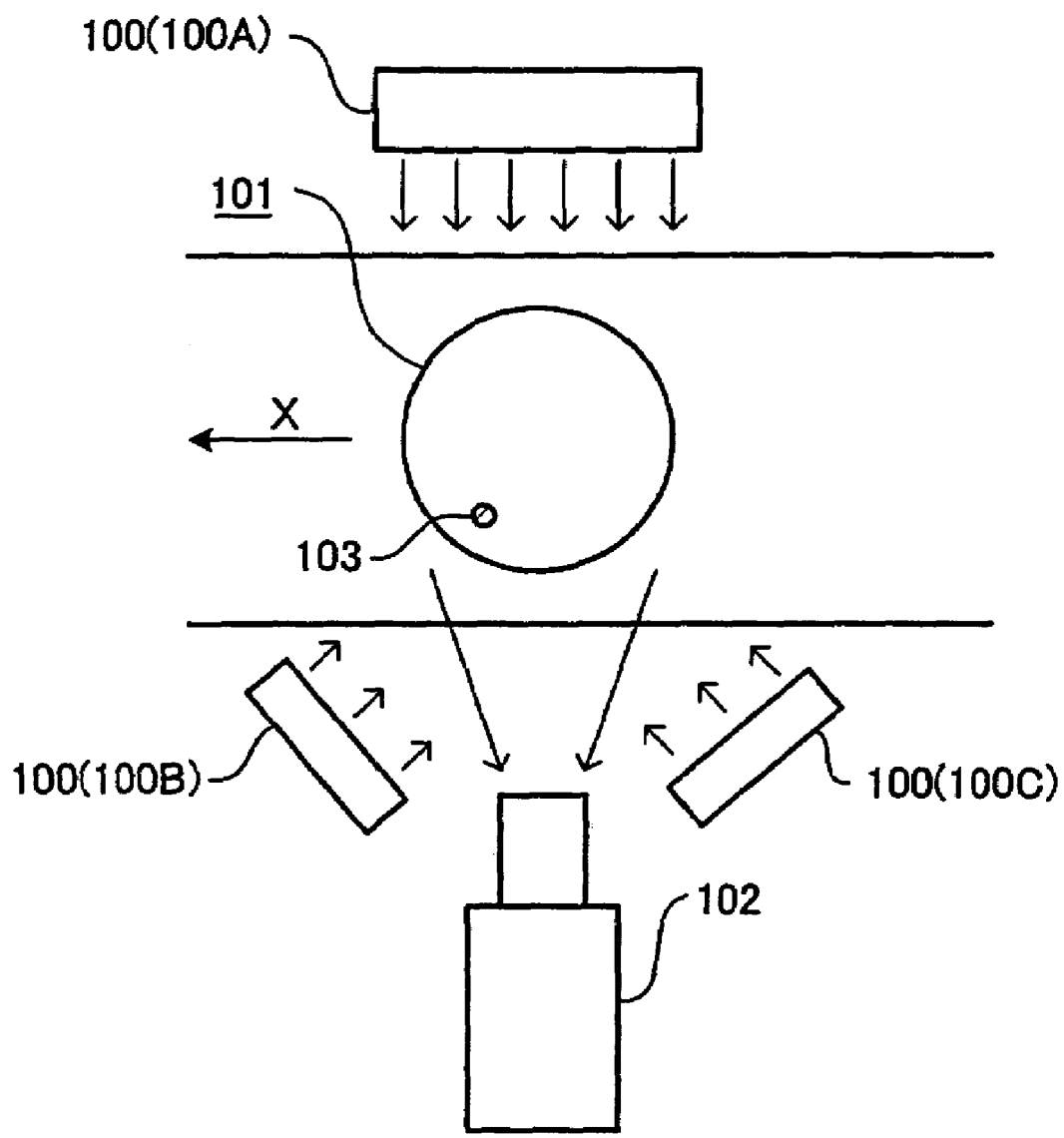
FIG. 4 is a structural view showing a second example of conventional inspecting apparatus for a foreign matter.
Figure 5:
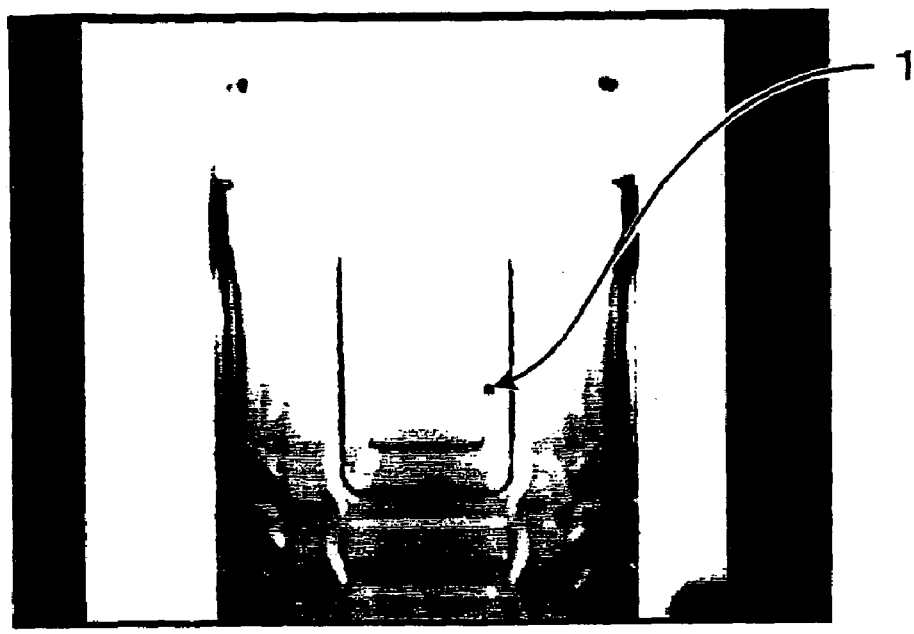
FIG. 5 shows a photographic image of an exemplary picked-up image (raw data) by the inspecting apparatus for a foreign matter of FIG. 4.
Figure 6:
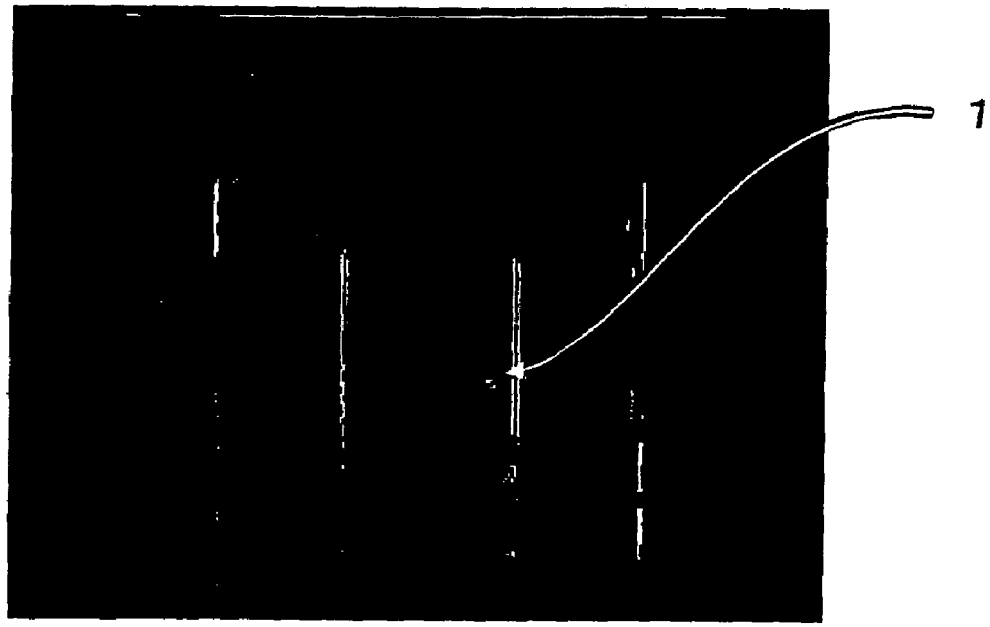
FIG. 6 shows an image produced by binarizing the picked-up image of FIG. 5.
Figure 14:
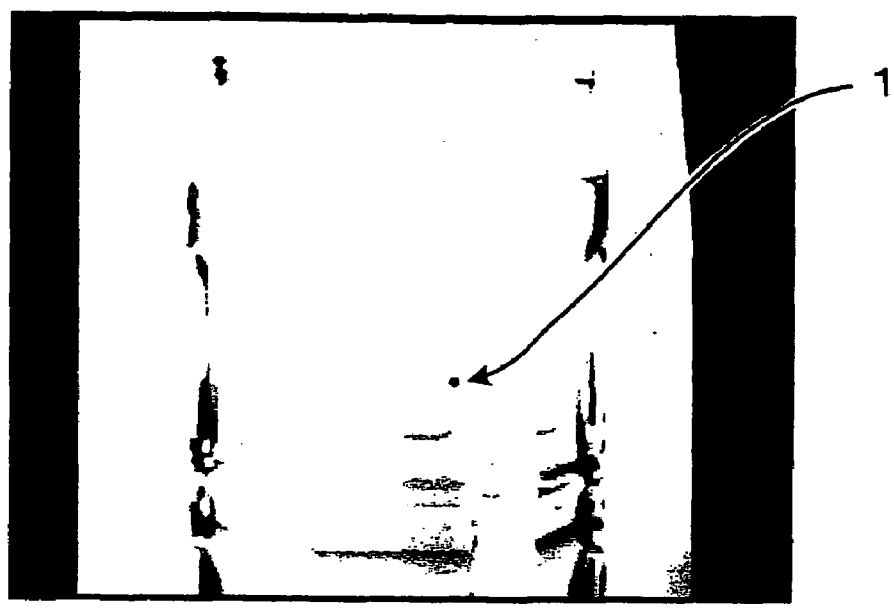
FIG. 14 shows a photographic image of an exemplary picked-up image (raw data) according to this invention.
Figure 15:
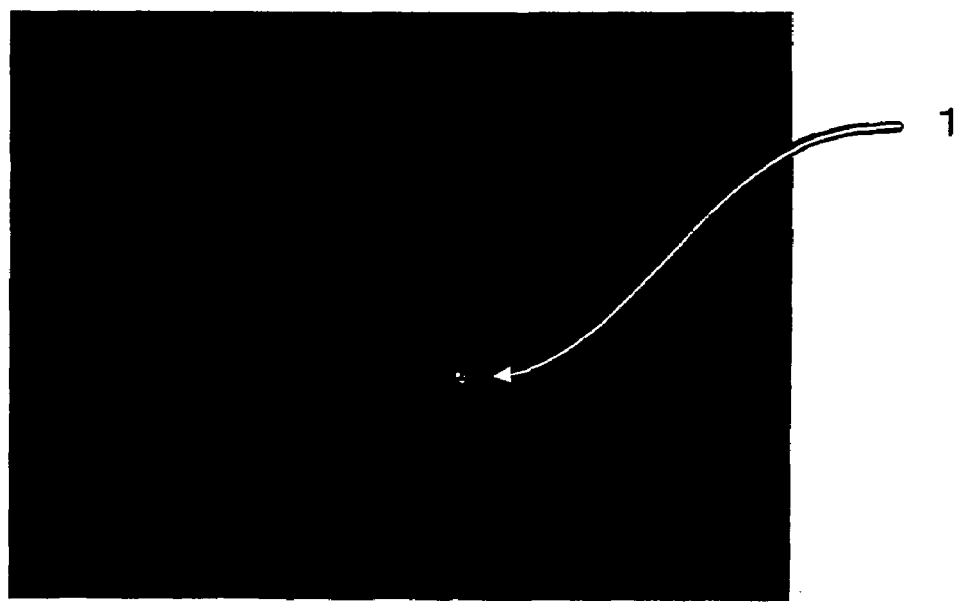
FIG. 15 shows an exemplary processed image (binary data) according to this invention.

By employing such an inspection technique, it is possible to securely detect a foreign matter contained in a liquid product in a container, at a high speed without stopping the production and irrespective of the shape and direction of the container. FIGS. 14 and 15 show an exemplary picked-up image and an exemplary processed image according to this invention. According to this invention, the outer shape line or the like of the container is eliminated from an image captured by the CCD sensor 30 as the image pickup unit and image information (raw data) as shown in FIG. 14 is acquired. FIG. 14 shows an image in the case where a transparent PET bottle is filled with transparent liquid. As such image information is binarized by the image processing unit 41, a binary image as shown in FIG. 15 is acquired and only a foreign matter is clearly shown. FIGS. 14 and 15 correspond to the image of a PET bottle (FIG. 5) captured by the foreign matter inspection technique on the straight line shown in FIG. 4 and its binary image (FIG. 6), respectively. In this invention, the recessed and protruding part of the container and the contour part of the container that cannot be completely eliminated by the conventional technique is perfectly eliminated after the binarization, and it can be seen that an image of a foreign matter only can be acquired.

According to this invention, no blind spot exists in the light casting area on the inspection subject and in the fields of view of the image pickup units, and no matter which direction the carried inspection subject faces having a recessed and protruding shape on its lateral part, images from which the recessed and protruding shape of the container and its contour part have been eliminated is formed when the inspection subject is captured from the viewing directions of the image pickup units. Therefore, the recessed and protruding shape of the container and its contour part that cannot be completely eliminated by the conventional optical inspection technique for a foreign matter on a straight line can be eliminated and even a very small foreign matter can be securely detected without making any misjudgment. Moreover, since all the products can be inspected without stopping the high-speed mass production line and defective products containing foreign matters can be securely detected and eliminated at the final stage, further security of the products can be achieved.

In summary, this invention discloses an inspecting apparatus for a foreign matter that can detect a foreign matter contained in a liquid product in a container securely and at a high speed even when a cylindrical container having a recessed and protruding shape on its lateral side or a rectangular container is tin inspection subject. The apparatus includes: illumination units that are arranged annularly on inner and outer sides of an annular carrier line having a setting part provided on a star wheel rotationally driven at a high speed, and that cast a luminous flux including parallel rays onto the lateral side of the inspection subject from plural directions around the inspection subject; image pickup units that are arranged on the outer side of the annular carrier line and that receive transmitted light and reflected light from the inspection subject, simultaneously from two directions around the inspection subject, and respectively pick up images of the lateral side of the inspection subject; and an inspection unit that inspects the existence of the foreign matter on the basis of image signals from the image pickup units; wherein the first and second image pickup units respectively pick up images of the inspection subject in a state where an angle θ1 formed by light-receiving axes of the first and second image pickup units is 30 to 90 degrees and an angle θ2 formed by the light-receiving axis of the image pickup unit and the luminous flux of the illumination unit next to the image pickup unit is 30 to 60 degrees.

What is claimed is:

1. An inspecting apparatus for detecting foreign matter in a liquid within a container having a shape with recesses and protrusions, wherein the liquid is an object of inspection wherein said container is being sequentially set upright in each mounting part provided on an annular carrier line of a star wheel that is rotationally driven in synchronization with carrier speed on a production line, any foreign matter in the liquid in said container being inspected while said container is carried at a high speed along the annular carrier line in the form of coaxial and equal-speed rotation with the star wheel, the apparatus comprising:

a plurality of illumination units that are arranged annularly on inner and outer sides of the annular carrier line having the mounting part provided on its circumference, to surround the lateral side of said container the inspection subject, and that cast a luminous flux substantially perpendicular to a vertical cross section of said container and including parallel rays, as illumination light, onto the lateral side of said container from a plurality of directions around said container;

first and second image pickup units that are arranged on the outer side of the annular carrier line and that simultaneously receive transmitted light and reflected light from said container illuminated by the illumination units, from two directions around said container, and respectively pick up images of the lateral side of said container; and an inspection unit that inspects the existence of a foreign matter in the liquid sealed in said container on the basis of image signals of the first and second image pickup units;

wherein the first and second image pickup units respectively pick up images of the inspection subject in a state where an angle θ1 formed by light-receiving axes of the first and second image pickup units is 30 to 90 degrees and an angle θ2 formed by the light-receiving axis of each image pickup unit and the luminous flux of the illumination unit next to each image pickup unit is 30 to 60 degrees.

2. The inspecting apparatus for a foreign matter according to claim 1, wherein the illumination unit arranged on the outer side of the annular carrier line includes a first illumination unit situated at a central part between the first and second image pickup units, a second illumination unit situated at a position opposite to the first illumination unit with respect to the first image pickup unit between them, and a third illumination unit situated at a position opposite to the first illumination unit with respect to the second image pickup unit between them.

3. The inspecting apparatus for a foreign matter according to claim 1, wherein the angle θ1 is substantially 90 degrees.

4. The inspecting apparatus for a foreign matter according to claim 2, wherein when an angle formed by the light-receiving axis of the first image pickup unit and a luminous flux of the second illumination unit is θ2$a$ and an angle formed by the light-receiving axis of the second image pickup unit and a luminous flux of the third illumination unit is θ2$b$, θ2$a$=θ2$b$ holds, which is equal to substantially 45/2 degrees.

5. The inspecting apparatus for a foreign matter according to claim 1, wherein the illumination unit arranged on the inner side of the annular carrier line includes a first illumination unit arranged to face the first image pickup unit and a second illumination unit arranged to face the second image pickup unit.

6. The inspecting apparatus for a foreign matter according to claim 1, wherein the setting part is formed by a translucent member, and wherein the apparatus further comprises an illumination unit that casts a luminous flux including parallel rays perpendicularly to a bottom side of said container from below the setting part.

7. An inspection method for detecting foreign matter in a liquid within a container having a shape with recesses and protrusions, wherein said container being sequentially set upright in each mounting part provided on an annular carrier line of a star wheel that is rotationally driven in synchronization with carrier speed on a production line, any foreign matter in the liquid sealed in said container is inspected while said container is carried at a high speed along the annular carrier line in the form of coaxial and equal-speed rotation with the star wheel, the method comprising:

arranging respectively a plurality of illumination units annularly on inner and outer sides of the annular carrier line to surround the lateral side of said container, and first and second image pickup units on the outer side of the annular carrier line in a state where an angle θ1 formed by light-receiving axes of the first and second image pickup units is 30 to 90 degrees and an angle θ2 formed by the light-receiving axis of each image pickup unit and a luminous flux of the illumination unit next to each image pickup unit is 30 to 60 degrees; and irradiating a the luminous flux substantially perpendicular to a vertical cross section of said container and including parallel rays, as illumination light, onto the lateral side of said container from a plurality of directions around said container by a plurality of illumination units, receiving transmitted light and reflected light from said container illuminated by the illumination units, from two directions around said container, and picking up images of the lateral side of said container by the first and second image pickup units;

processing each image signal outputted from said first and second image pickup units; and detecting the existence of a foreign matter contained in the liquid including a foreign matter existing in the liquid in near insides of the recesses and protrusions of said container and the contour of said container, and a floating matter in the liquid.

8. An inspecting apparatus for detecting foreign matter in a liquid within a container, the apparatus comprising:

a plurality of illumination units arranged to cast a luminous flux onto said container;

first and second image pickup units arranged to obtain images of the container; and an inspection unit adapted to perform image processing on the obtained images of the container to find a foreign matter in the liquid within the container.

* * * * *